(12) United States Patent
Kazutoh et al.

(10) Patent No.: US 6,380,245 B1
(45) Date of Patent: *Apr. 30, 2002

(54) ANTIBIOTICS TKR1912-I AND TKR1912-II AND PROCESS FOR PRODUCING THE SAME

(75) Inventors: Takesako Kazutoh, Otsu; Yoshie Yoshikawa, Kyoto; Eiko Koyama, Uji; Tomoko Masuda, Otsu; Ikunoshin Kato, Uji, all of (JP)

(73) Assignee: Takara Shuzo Co., Ltd., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/550,053

(22) Filed: Apr. 14, 2000

Related U.S. Application Data

(63) Continuation-in-part of application No. 08/913,250, filed as application No. PCT/JP96/00565 on Mar. 8, 1996, now Pat. No. 6,068,839.

(30) Foreign Application Priority Data

Mar. 10, 1995 (JP) ................................................ 7-79756

(51) Int. Cl.$^7$ ........................ A61K 31/34; A61K 35/00; C07D 307/16; C12M 11/18
(52) U.S. Cl. ........................ 514/461; 549/485; 424/116; 435/171
(58) Field of Search ........................ 435/171; 424/116; 549/485; 514/461

(56) References Cited

FOREIGN PATENT DOCUMENTS

| EP | 0 170 006 A2 | 2/1986 |
|---|---|---|
| EP | 0 352 092 A2 | 1/1990 |
| JP | 57-32286 | 2/1982 |
| WO | WO96/28456 | 9/1996 |

OTHER PUBLICATIONS

XP–002138911, Takesako et al, Aureobasidins, New Antifungal Antibiotics Taxonomy, Fermentation, Isolation, and Properties, The Journal of Antibiotics, vol. 44, No. 9, Sep. 1991, pp. 919–924.

XP 000578251, Yoshikawa et al, Isolation, Structures, and Antifungal Activities of New Aureobasidins, The Journal of Antibiotics, vol. 46, No. 9, Sep. 1993, pp. 1347–1354.

XP–000907491, McCormack et al, Production Of Antibacterial Compounds by Phylloplane–Inhabiting Yeasts and Yeastlike Fungi, Applied and Environmental Microbiology, vol. 60, No. 3, Mar. 1994, pp. 927–931.

*Primary Examiner*—Jerome D. Goldberg
(74) *Attorney, Agent, or Firm*—Connolly Bove Lodge & Hutz

(57) ABSTRACT

The present invention relates to novel antibiotics TKR1912-I having the following formula I and TKR1912-II having the following formula II or pharmacologically acceptable salts thereof, which are useful as a remedy for fungal infections, as well as a process for producing them and a microorganism capable of producing them.

7 Claims, 9 Drawing Sheets

US 6,380,245 B1

ANTIBIOTICS TKR1912-I AND TKR1912-II AND PROCESS FOR PRODUCING THE SAME

This is a continuation-in-part (CIP) application of Ser. No. 08/913,250, filed Jul. 10, 1998, now U.S. Pat No. 6,068,839, which is a U.S. National Phase application of International Application No. PCT/JP96/00565, filed Mar. 8, 1996.

TECHNICAL FIELD

The present invention relates to TKR1912-I and TKR1912-II, which are antibiotics of use as therapeutic agents for fungal infections diseases, a method for their production, and microorganisms producing said antibiotics.

BACKGROUND ART

Fungi are known to cause a variety of infectious diseases in man, animals, and plants. In man, for instance, they cause superficial mycosis affecting the skin, oral cavity, etc. and systemic mycosis affecting the viscera, brain, etc. They cause similar infections in pet and domestic animals as well. Furthermore, fungi inflict various hazardous effects on plants such as orchard trees and vegetables.

As the principal pathogenic fungi causing systemic mycosis in man, those of the genera Candida, Cryptococcus, and Aspergillus, among others, are known. As to superficial mycosis, candidal species affecting the skin, oral cavity, and vagina and trichophytons infecting the skin of the extremities are regarded as the major pathogenic fungi. Besides those fungi, many other fungi exist in the environment and are suspected to contaminate the animal and vegetable kingdoms.

As antimycotics of use for the prevention and treatment of such fungal infections and contaminations, only a very few are known. As therapeutic drugs for systemic mycosis in man and animals, for instance, amphotericin B, flucytosine, miconazole, and fluconazole can be mentioned. However, those compounds are not fully satisfactory in potency, toxic potential, or antifungal spectrum, thus being not impeccable as therapeutic drugs.

DISCLOSURE OF THE INVENTION

In view of the above-mentioned prior art, the present invention has for its object to provide a novel class of antibiotics which are of value as therapeutic agents for fungal infections.

In their search for a novel antibiotic, the inventors of the present invention isolated a large number of microorganisms from the natural kingdom, isolated the antibiotics they produced, and scrutinized their biological properties. As a result, they discovered that the culture broth of a strain of microorganism of the genus Aureobasidium contained an antibiotic having antifungal activity against pathogenic fungi inclusive of Candida albicans and Cryptococcus neoformans. Accordingly the inventors isolated this antibiotic and studied its physicochemical properties. As a result, they discovered that the above antibiotic is actually comprised of two novel substances having distinct physicochemical characteristics and named them TKR1912-I and TKR1912-II. The present invention provides the above-mentioned antibiotics TKR1912-I and TKR1912-II and a method for their production.

DETAILED DESCRIPTION OF THE INVENTION

The present invention is now described in detail.

The antibiotic TKR1912-I of the invention has the following physicochemical characteristics (1), (2), (3), (4), and (5).
(1) A fast atom bombardment mass spectrum (FAB-MS) with a peak at m/z559 [M+H]$^+$;
(2) a carbon number of 26, an oxygen number of 13, and a nitrogen number of 0;
(3) an ultraviolet absorption spectrum in methanol with the terminal absorptions shown in FIG. 1;
(4) an infrared absorption spectrum according to the KBr method with the dominant absorption wavenumbers of 3430 $cm^{-1}$, 2920 $cm^{-1}$, 2850 $cm^{-1}$, 1740 $cm^{-1}$, and 1190 $cm^{-1}$ as shown in FIG. 2; and
(5) soluble in methanol, chloroform, and water and practically insoluble in hexane.

The antibiotic TKR1912-II of the invention has the following physicochemical characteristics (6), (7), (8), (9), and (10).
(6) A FAB-MS with a peak at m/z585 [M+H]$^+$.
(7) a carbon number of 28, an oxygen number of 13, and a nitrogen number of 0;
(8) an ultraviolet absorption spectrum in methanol with the terminal absorptions shown in FIG. 3;
(9) an infrared absorption spectrum according to the KBr method with the dominant wavenumbers of 3440 $cm^{-1}$, 2920 $cm^{-1}$, 2850 $cm^{-1}$, 1740 $cm^{-1}$, and 1200 $cm^{-1}$ as shown in FIG. 4; and
(10) soluble in methanol, chloroform, and water and practically insoluble in hexane.

Figure 5:
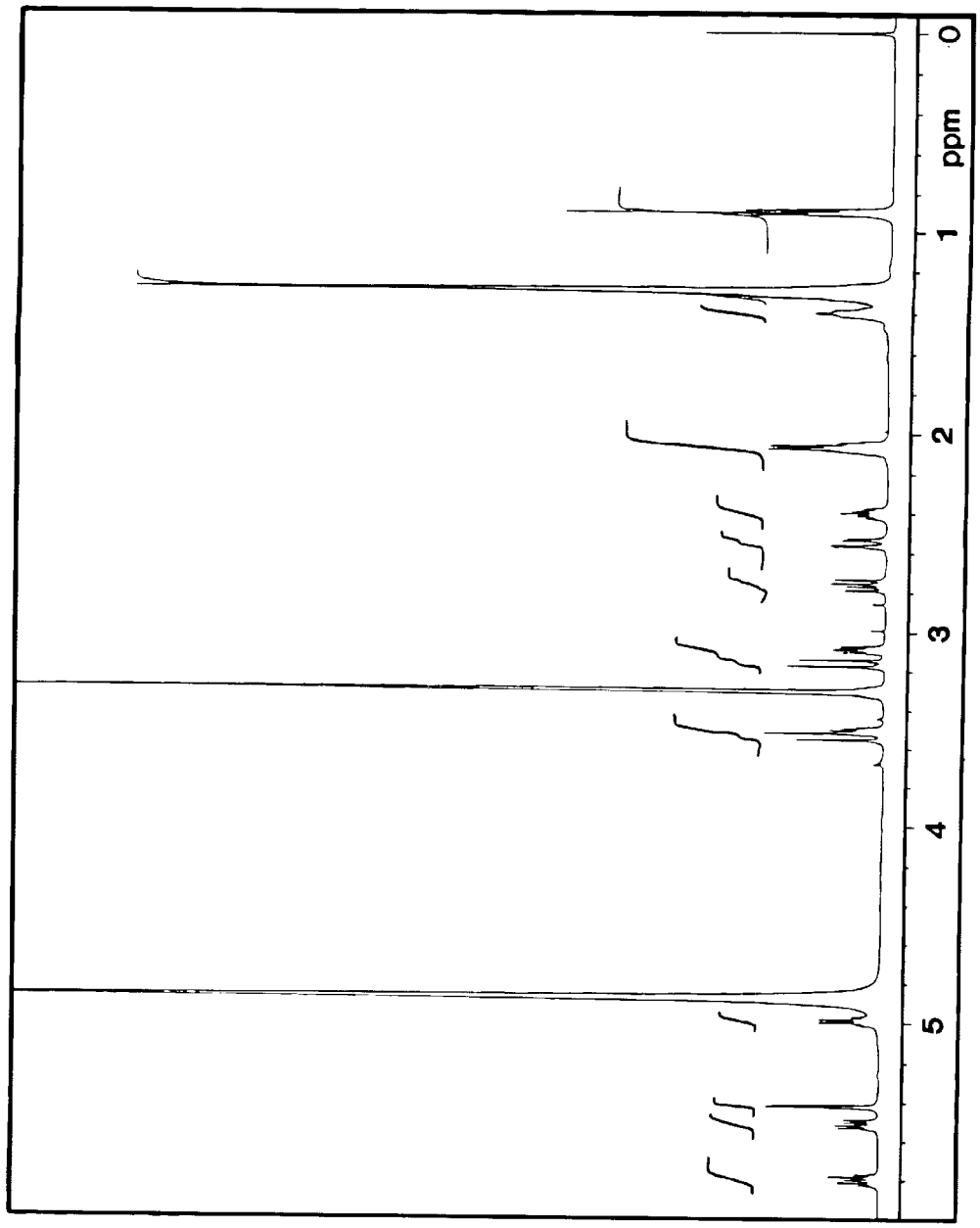
FIG. 5 is a chart showing the $^1$H-NMR spectrum of the antifungal substance TKR1912-I, in which the abscissa represents chemical shift (ppm)
Figure 6:
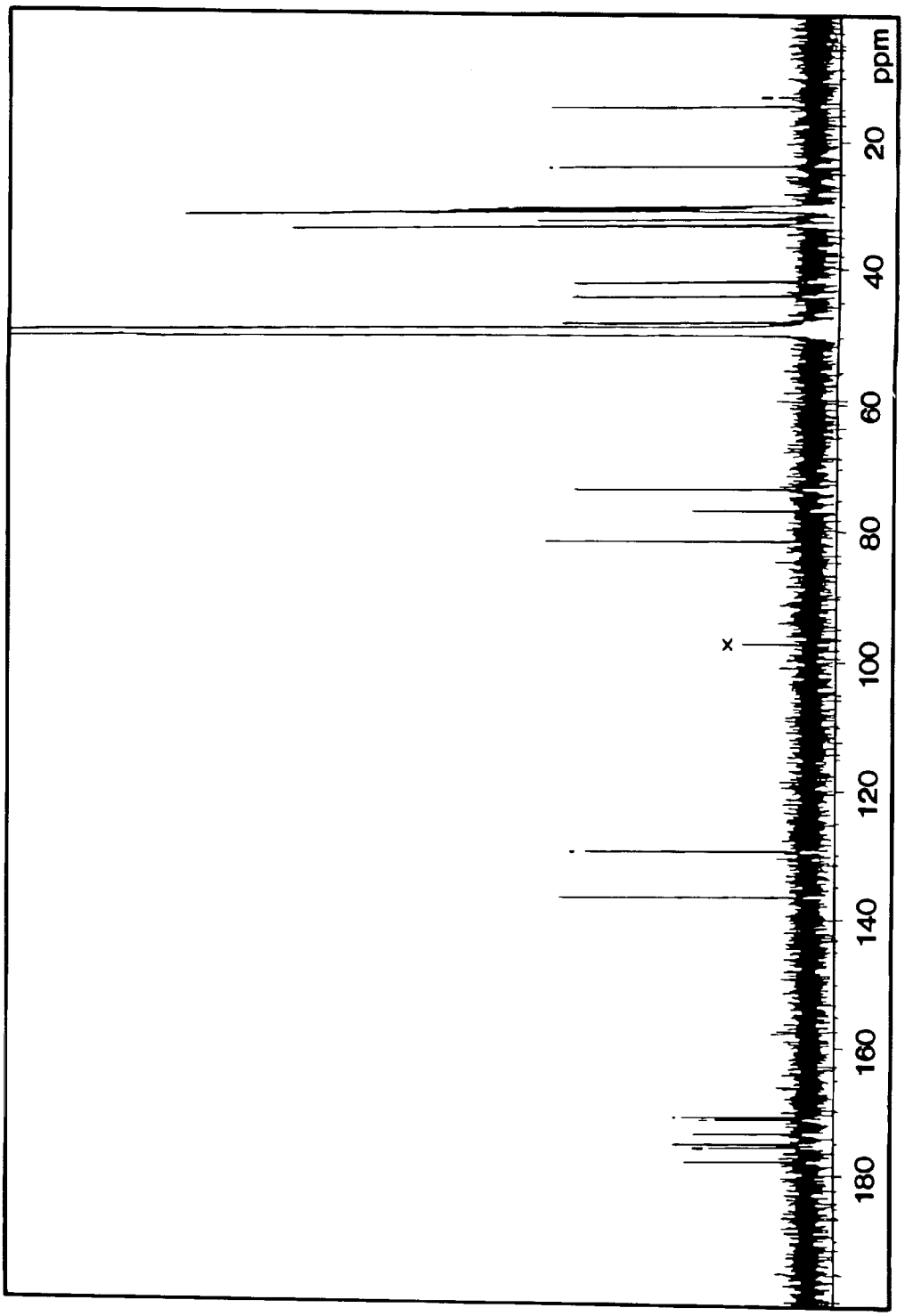
FIG. 6 is a chart showing the $^{13}$C-NMR spectrum of the antifungal substance TKR1912-I, in which the abscissa represents chemical shift (ppm)
Figure 9:
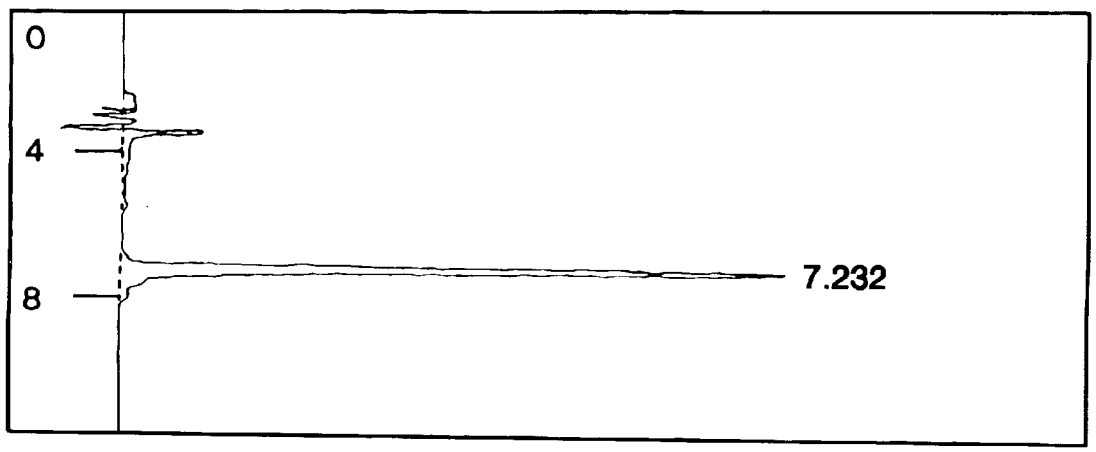
FIG. 9 is a HPLC chart of the antifungal substance TKR1912-I showing its elution position, in which the ordinate represents relative UV intensity at 220 nm and the abscissa represents retention time (min.)

Furthermore, TKR1912-I mentioned above has the $^1$H-NMR spectrum shown in FIG. 5 and the $^{13}$C-NMR spectrum shown in FIG. 6, and is characterized in that, in reversed-phase partition high-performance liquid chromatography, it is eluted in the position indicated in FIG. 9.

Figure 7:
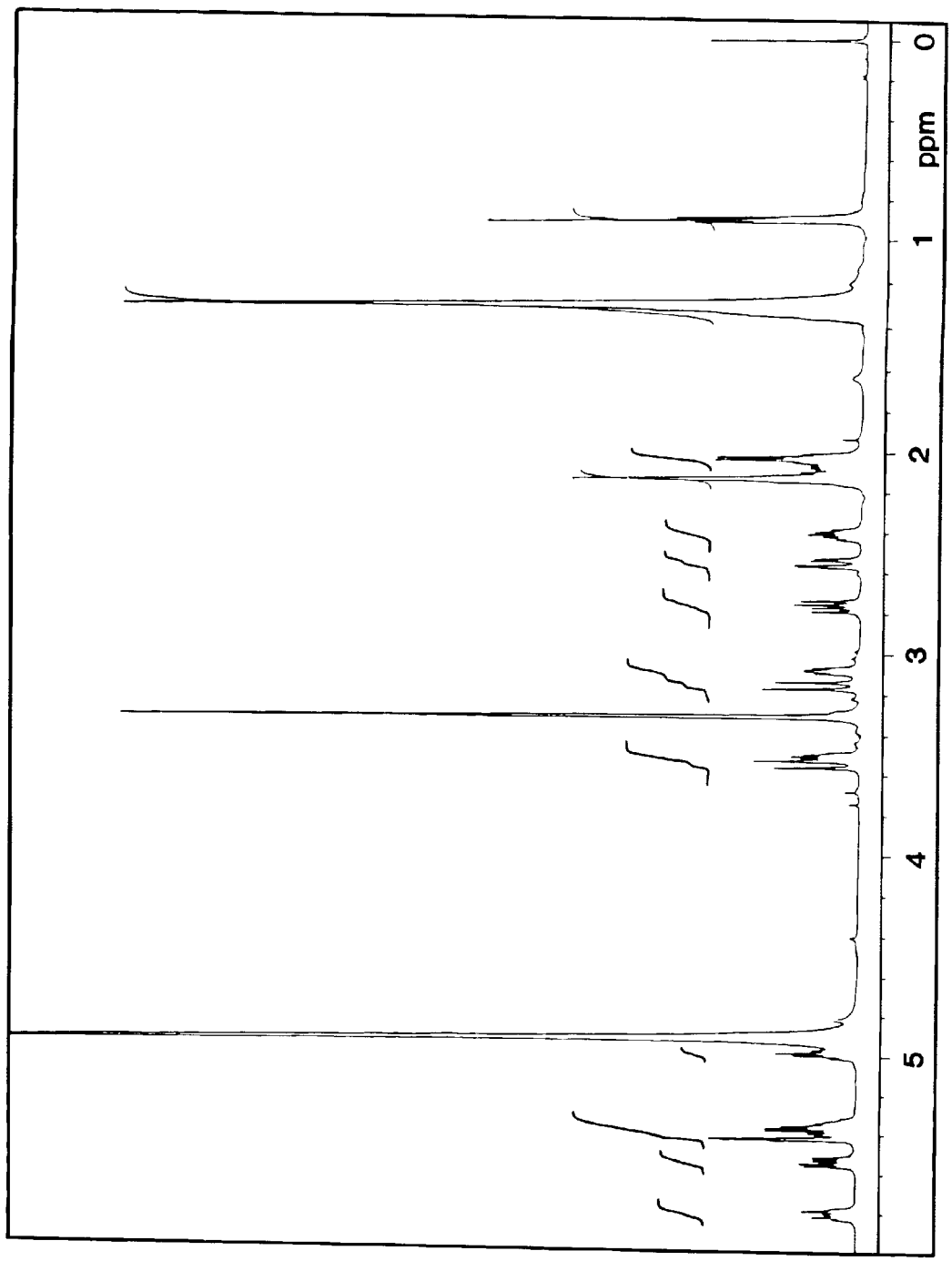
FIG. 7 is a chart showing the $^1$H-NMR spectrum of the antifungal substance TKR1912-II, in which the abscissa represents chemical shift (ppm)
Figure 8:
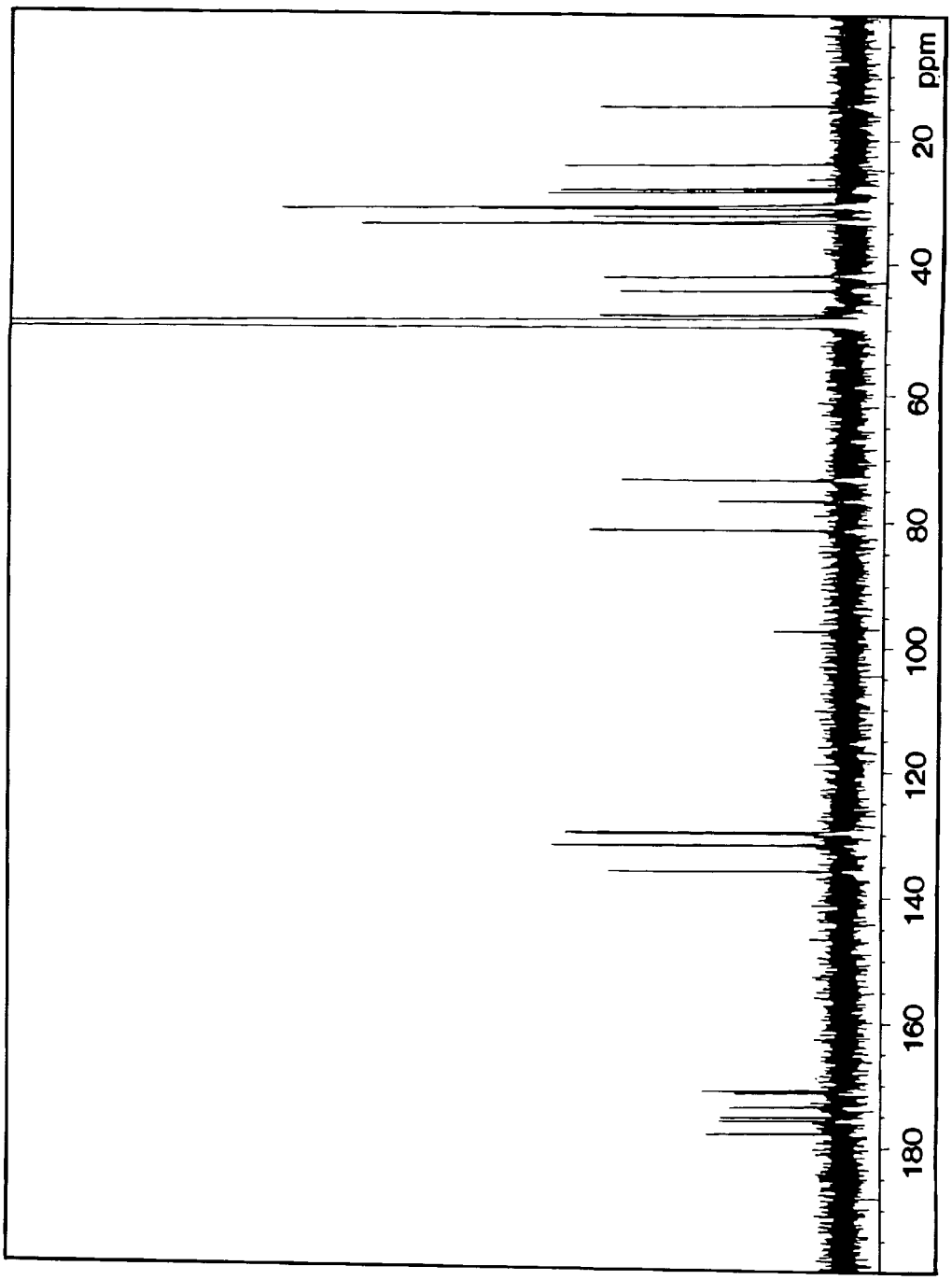
FIG. 8 is a chart showing the $^{13}$C-NMR spectrum of the antifungal substance TKR1912-II, in which the abscissa represents chemical shift (ppm)
Figure 10:
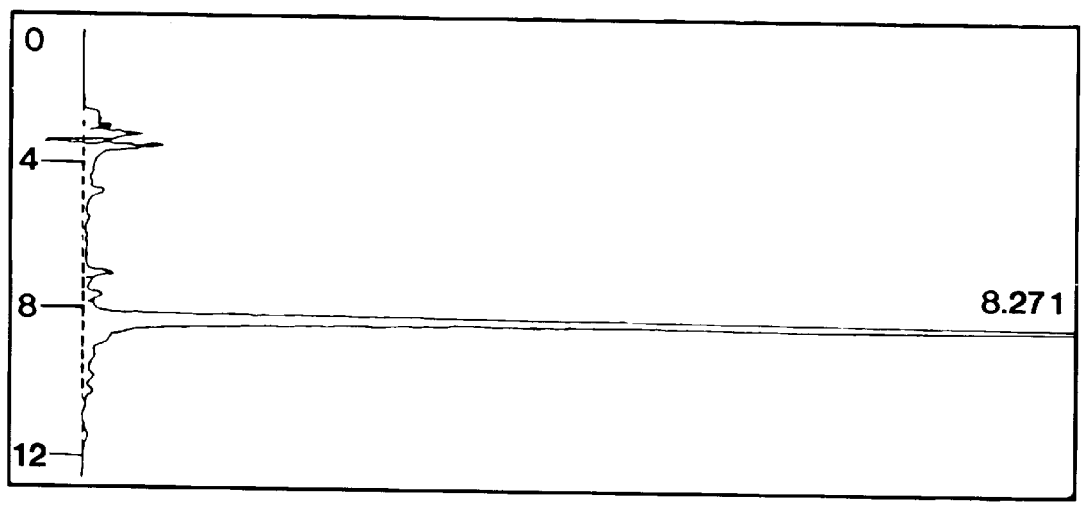
FIG. 10 is a HPLC chart of the antifungal substance TKR1912-II showing its elution position, in which the ordinate represents relative UV intensity at 220 nm and the abscissa represents retention time (min.)

On the other hand, TKR1912-II mentioned above has the $^1$H-NMR spectrum shown in FIG. 7 and the $^{13}$C-NMR spectrum shown in FIG. 8 and is characterized in that, in reversed-phase partition liquid chromatography, it is eluted in the position indicated in FIG. 10.

From the above physicochemical characteristics, TKR1912-I has been found to have the following formula I:

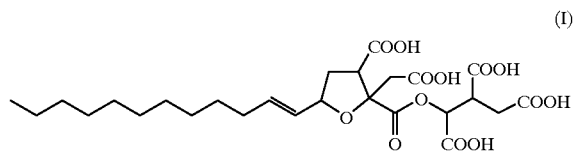

(I)

and TKR1912-II has been found to have the following formula II:

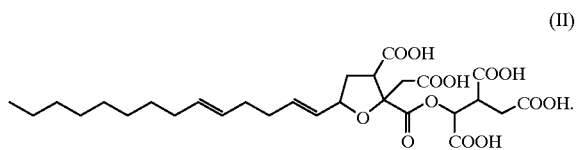

(II)

The above-mentioned TKR1912-I and TKR1912-II can be produced by growing a strain of microorganism belonging to the genus Aureobasidium and capable of producing said TKR1912-I and TKR1912-II in a culture medium and harvesting the respective substances from the resulting culture broth.

There is no limitation on the strain of microorganism that can be used in the present invention only provided it belongs to the genus Aureobasidium and is capable of producing said TKR1912-I and TKR1912-II. Thus, for example, Aureobasidium sp. TKR1912 strain (hereinafter referred to as the TKR1912 strain) can be mentioned.

The above-mentioned TKR1912 strain is a novel strain not heretofore described in the literature, and isolated and characterized for the first time by the inventors of the present invention. The strain has the property to produce TKR1912-I and TKR1912-II with advantage. The mycological characteristics of this TKR1912 strain are now described in detail.

The colonial colors of said TKR1912 strain on various media are shown in Table 1. The descriptions of colors in the table are based on those prescribed in Japanese Industrial Standard (JIS) Z 8102 (1985) and reflect the results of observation on days 4, 7 and 14 of culture at 25° C. after inoculation in the respective media.

TABLE 1

| Medium | Colony diameter (mm) | Color Day 4 | Day 7 | Day 14 |
| --- | --- | --- | --- | --- |
| Malt extract agar | 75 | Pale yellow-red 5YR9/2 | Olive 5GY4/3 | Olive 2.5GY4/2 |
| Potato dextrose agar | 45 | Pale yellow-red 5YR9/2 | Peach 5YR8/3 | Greenish brown 5Y4/3 |

TABLE 1-continued

| Medium | Colony diameter (mm) | Color Day 4 | Day 7 | Day 14 |
| --- | --- | --- | --- | --- |
| Sabouraud's agar | 44 | Pale yellow-red 5YR9/2 | Pale yellow 10YR9/3 | Dark yellow gray 5Y3/1 |
| YpSs agar | 34 | Pale yellow-red 5YR9/2 | Yellowish 7.5YR8/8 | Yellowish 7.5YR8/8 |

The above TKR1912 strain grows luxuriously on malt extract agar, potato dextrose agar, and Sabouraud's agar etc. and its colony is glistening in the center and generally viscous or pasty but may become leathery on aging. The color of the colony is white in an initial phase of culture, then locally turns pale yellow-red to peach- or apricot-color but in due course becomes olive to greenish brown. As days further pass by, the colony color becomes tan to blackish tan. The pigments are insoluble.

The hyphae measure 2 to 3 μm in diameter and are well developed but not forming an aerial mycelium but extending into the substrate agar. Frequently emergent from the tip or side of the hypha are conidia sized 2 to 4×3 to 8 μm in the manner of fingertips, with some of them growing into a ball-like mass. Young vegetative cells are yeast-like, sized 2 to 4×8 to 14 μm, and either ellipsoidal or lemon-shaped, and multiply by polycentric budding. It forms arthrospores sized 4 to 10×8 to 20 μm and chlamydospores measuring 4 to 8×8 to 14 μm. No ascospore is formed.

Among the mycological characteristics of the TKR1912 strain, its physiological characteristics are as follows. Temperature range for growth: 10° C. to 30° C. The optimum range for growth is around 25° C.

pH range for growth: pH 2 to pH 9. The optimum range is pH 3 to pH 7.

Pigment production: Insoluble melanoid pigments are produced.

Based on the above mycological characteristics, the strain was compared with the species of the genus Aureobasidium as described in W. B. Cooke, Mycopathologia et Mycologia Applicata, 17, 1 to 43, 1962; J. A. von Arx, The Genera of Fungi Sporulating in Pure Culture, J. Cramer Lehre; and E. J. Hermanides-Nijhoff, Studies in Mycology, No. 15, 141 to 166, CBS. Baarn, 1977), among other literature. As a result, the above TKR1912 strain was identified to be a fungal strain belonging to the genus Aureobasidium.

However, there has been no report on a fungus ever having TKR1912-I or TKR1912-II-producing ability among the hitherto-reported strains of the genus Aureobasidium. Therefore, the inventors of the present invention considered it to be a novel strain and deposited it with the National Institute of Bioscience and Human Technology, Department of Trade and Industry (address: 1–3, Tsukuba-shi Higashi 1-chome, Ibaraki, ZIP code 305) under the accession number of FERM BP-5368 (the date of original deposit: Feb. 15, 1995, the date of request for international deposit: Jan. 19, 1996).

The present invention can be carried into practice not only with the above-mentioned TKR1912 strain but also with any spontaneous or artificial mutant of said TKR1912 strain or any other strain of microorganism belonging to the genus Aureobasidium and capable of producing TKR1912-I and/or TKR1912-II.

In accordance with the present invention, TKR1912-I and TKR1912-II are produced by cultivating a TKR1912-I/

TKR1912-II-producing strain in a nutrient medium. Nutrients to be used for the medium include various carbon sources such as glucose, fructose, saccharose, starch, dextrin, glycerol, molasses, malt syrup, oils and fats, and organic acids.

Nitrogen sources as nutrients include organic and inorganic nitrogenous substances such as soybean meal, cottonseed meal, corn steep liquor, casein, peptone, yeast extract, meat extract, wheat germs, urea, amino acids, ammonium salts, etc. Salts as nutrients are various inorganic salts such as salts of sodium, potassium, calcium, magnesium, etc. and salts of phosphoric acid. Those substances can be used independently or in a suitable combination.

Where necessary, the nutrient medium may be supplemented with heavy metal salts such as iron salts, copper salts, zinc salts, cobalt salts, etc., vitamins such as biotin, vitamin $B_1$, etc., and other organic and inorganic substances which would assist in growth of the microorganism and promote production of TKR1912-I and TKR1912-II.

In addition to the above components, an antifoamer and/or a surfactant, for example silicone oil, polyalkylene glycol ethers, etc., can be added to the nutrient medium.

In cultivating a strain of microorganism capable of producing TKR1912-I/TKR1912-II in said nutrient medium, a variety of cultural methods which are generally used in the production of antibiotics by means of microorganisms can be employed. However, liquid culture, particularly shake culture or submerged aerobic culture, is preferred.

The cultivation is preferably carried out at 15° C. to 30° C. The pH of the medium may range from pH 2 to pH 8 but is preferably around pH 4. Regarding the incubation time, generally a sufficient output of the antibiotic can be expected by 1 to 6 days of culture.

By the above cultivation, TKR1912-I and TKR1912-II are contained both intracellularly and extracellularly and accumulated in the culture broth. In the present invention, the TKR1912-I and TKR1912-II accumulated in the culture broth can be recovered and isolated from the broth by utilizing their physicochemical characteristics and, where necessary, by further purification.

The above-mentioned recovery can be achieved by extracting the whole broth with a non-hydrophilic organic solvent such as ethyl acetate, butyl acetate, chloroform, butanol, methyl isobutyl ketone, or the like. As an alternative, it is possible to subject the broth to centrifugation or filtration to separate into the medium and microorganisms and isolate the antibiotics from each of the medium and microorganisms.

The TKR1912-I and TKR1912-II can be separated from the medium not only by the above-mentioned extraction method using a non-hydrophilic organic solvent but also by the method which comprises contacting the medium with an adsorbent to let TKR1912-I and TKR1912-II adsorbed on the adsorbent and desorbing or eluting them with a solvent. The adsorbent that can be used includes, for example, activated carbon, cellulose powder, and adsorbent resins. As the above-mentioned solvent, a variety of solvents can be selectively used according to the kind and properties of the adsorbent and either singly or in combination. Thus, an aqueous solution of one or more water-soluble organic solvents, such as aqueous acetone, aqueous alcohol, etc., can be employed. For separation of TKR1912-I and TKR1912-II from the microorganisms, the extraction technique using a hydrophilic organic solvent such as acetone can be employed.

In the present invention, the crude extract of TKR1912-I and TKR1912-II can be purified by the conventional techniques for the separation purified of hydrophobic antibiotics, e.g. by column chromatography or high-performance liquid chromatography, using a column packed with a stationary phase such as silica gel, activated alumina, activated charcoal, adsorbent resin, etc. The eluent that can be used for silica gel column chromatography includes chloroform, ethyl acetate, methanol, acetone, water, mixtures thereof, etc.

The stationary phase for high-performance liquid chromatography includes but is not limited to chemically derivatized silica gel, such as silica gel derivatives having octadecyl, octyl, or phenyl groups, and polystyrenic porous polymer gels, while the mobile phase that can be used includes aqueous solutions of water-soluble organic solvents, such as aqueous methanol, aqueous acetonitrile, etc.

The TKR1912-I and TKR1912-II can each be put to use as such or in the form of a pharmacologically acceptable salt in medicinal applications.

There is no particular limitation on the type of pharmacologically acceptable salt. Thus, the salt includes salts of mineral acids such as hydrochloric acid, sulfuric acid, nitric acid, phosphoric acid, hydrofluoric acid, hydrobromic acid, etc., salts of organic acids such as formic acid, acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, camphorsulfonic acid, etc., and salts of alkali metals or alkaline earth metals, such as sodium, potassium, calcium, etc.

To administer the TKR1912-I or TKR1912-II or their pharmacologically acceptable salts, as a drug, they can be administered either as such or in the form of a pharmaceutical composition containing typically 0.1 to 99.5%, preferably 0.5 to 90% thereof in a pharmaceutically acceptable, non toxic and inert carrier to animals inclusive of humans.

The carrier mentioned above includes solid, semisolid or liquid diluents, fillers, other formulation auxiliaries, etc. and such carriers can be used alone or in combination.

The above-mentioned pharmaceutical composition is preferably administered in unit dosage forms and can be administered orally, parenterally, topically (e.g. transdermally) or rectally. Of course, those pharmaceutical compositions should be administered in dosage forms suited for the respective route of administration.

For administration of TKR1912-I or TKR1912-II, or their pharmacologically acceptable salts, as a drug, the dose as an antifungal agent is preferably selected with reference to patient factors such as age and body weight, route of administration, nature and severity of disease, etc. Usually in man, however, the daily dose of the active ingredient for an adult patient is 10 to 2000 mg. While a daily dose lower than the above range may be sufficient in some cases, a dose higher than the range may be required in other cases. When a high dose is used, the daily dosage is preferably administered in several divided doses.

The oral administration can be made using solid, powdery, or liquid dosage forms such as bulc powders, powders, tablets, dragees, capsules, drops, subligual tablets, etc.

For the parenteral administration, liquid unit dosage forms for subcutaneous, intramuscular, or intravenous administration, typically solutions and suspensions, can be employed. These preparations can be manufactured by suspending or dissolving a predetermined amount of TKR1912-I or TKR1912-II, or a pharmaceutically acceptable salt thereof, in a non toxic liquid carrier suitable for injection, such as an aqueous medium or an oily medium, and sterilizing the resulting suspension or solution.

The topical administration (e.g. transdermal administration) can be carried out using a variety of topical dosage forms such as liquids, creams, powders, pastes, gels, and ointments. These dosage forms can be manufactured by using a predetermined amount of TKR1912-I or TKR1912-II, or a pharmacologically acceptable salt thereof, in combination with one or more of the perfume, coloring agent, filler, surfactant, humectant, emollient, gelatinizer, carrier, preservative, stabilizer, etc., suitable for topical dosage formulations.

The rectal administration can be made using, for example, suppositories each mixing a predetermined amount of TKR1912-I or TKR1912-II, or their pharmacologically acceptable salts, with a low-melting solid base such as higher esters, e.g. myristyl palmitate, polyethylene glycol, cacao butter, or a mixture of them.

BEST MODE OF CARRYING OUT THE INVENTION

The following examples are further illustrative of the present invention, but by no means limitative of the scope of the invention.

EXAMPLE 1

A loopful of TKR1912 strain (FERM P-14759) from a slant culture was used to inoculate into a 500 ml Erlenmeyer flask containing 100 ml of liquid medium (Difco potato dextrose broth, 2.4% (w/v)) and incubated on a shaker at 25° C. for 3 days to prepare a seed culture. This seed culture 1.0 ml was transferred to 24 Erlenmeyer flasks of 500 ml capacity each containing 125 ml of the same liquid medium as above and incubated (under shaking at 220 rpm) at 25° C. for 8 days. The obtained culture broth was centrifuged and the supernatant was separated from the microorganisms. The supernatant was adjusted to pH 2 and adsorbed on a column (2 L) of Diaion HP40 (Mitsubishi Kasei Corporation) equilibrated with water. After the column was rinsed with water, elution was carried out with 5 L of methanol to recover an active fraction. This fraction was concentrated under reduced pressure to recover 2.24 g of a residue.

The residue thus obtained was dissolved in 600 ml of water and the solution was adjusted to pH 8.7 and extracted twice with 600 ml of ethyl acetate each. The ethyl acetate layer thus obtained was concentrated to dryness under reduced pressure to recover 1.0 g of a residue. This residue was dissolved in 50 ml of methanol and subjected to preparative high-performance liquid chromatography to provide two active fractions. The high-performance liquid chromatography was carried out under the following conditions.

Apparatus: Delta Prep 4000 System (Waters)
Column: Soken Pack (8.0 cm×50 cm) (Soken Kagaku)
Mobile phase: 80 to 100% (v/v) acetonitrile/water The above fractions were respectively concentrated under reduced pressure to provide 32 mg of crude TKR1912-I and 172 mg of pure TKR1912-II as white powders. The crude TKR1912-I was further subjected to high-performance liquid chromatography to isolate an active fraction. This fraction was concentrated under reduced pressure to provide 13 mg of pure TKR-1912-I as white powders. This second high-performance liquid chromatography was carried out under the following conditions.

Apparatus: LC-8A (Shimadzu)
Column: YMC Pack (2.0 cm×25 cm) (YMC)
Mobile phase: 0.05% trifluoroacetic acid-containing 70% (v/v) acetonitrile/water Physicochemical Properties To confirm that the white powders obtained as above were TKR1912-I and TKR1912-II, respectively, the respective powders were physicochemically analyzed for characterization by mass spectrometry using JMS-DX302 mass spectrometer (Jeol Ltd.), $^1$H-NMR (in deuterated methanol with tetramethylsilane as reference) and $^{13}$C-NMR (with deuterated methanol as reference) using JNM-A500 nuclear magnetic resonance spectrometer (Jeol Ltd.), ultraviolet spectrophotometry (ca 30 µg/ml solution in MeOH) using UV-250 self-recording spectrophotometer (Shimadzu), and infrared absorption spectrometry (KBr method) using 270-30 infrared spectrophotometer (Hitachi).

(1) Mass Spectrometry

The purified white powdery product available upon vacuum concentration of the active fraction in said second high-performance liquid chromatography was found by FAB-MS to be a substance with a peak at m/z=559 $[M+H]^+$.

The purified white powdery product available upon vacuum concentration of the active fraction in said first high-performance liquid chromatography was found by FAB-MS to be a substance with a peak at m/z=585 $[M+H]^+$.

(2) Carbon Number and Nitrogen Number

The $^1$H-NMR and $^{13}$C-NMR determinations and analyses showed that the purified white powdery product available upon vacuum concentration of the active fraction in the second high-performance liquid chromatography had a carbon number of 26 and a nitrogen number of 0.

The $^1$H-NMR spectrum and $^{13}$C-NMR spectrum of this product are presented in FIG. 5 and FIG. 6, respectively.

The $^1$H-NMR and $^{13}$C-NMR determinations and analyses of the purified white powdery product available upon vacuum concentration of the active fraction in the first high-performance liquid chromatography revealed that it had a carbon number of 28 and a nitrogen number of 0.

The $^1$H-NMR spectrum and $^{13}$C-NMR spectrum of this product are presented in FIG. 7 and FIG. 8, respectively.

(3) Ultraviolet Absorption Spectra

Figure 1:
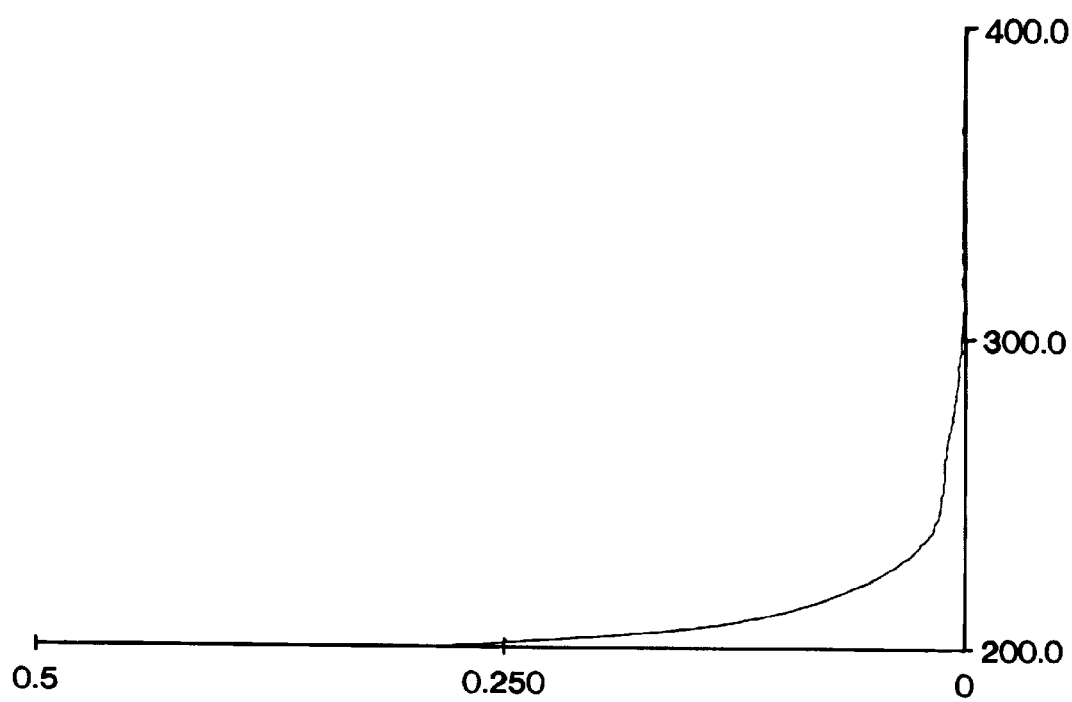
FIG. 1 is a chart showing the ultraviolet absorption spectrum of the antifungal substance TKR1912-I, in which the ordinate represents wavelength (nm)
Figure 2:
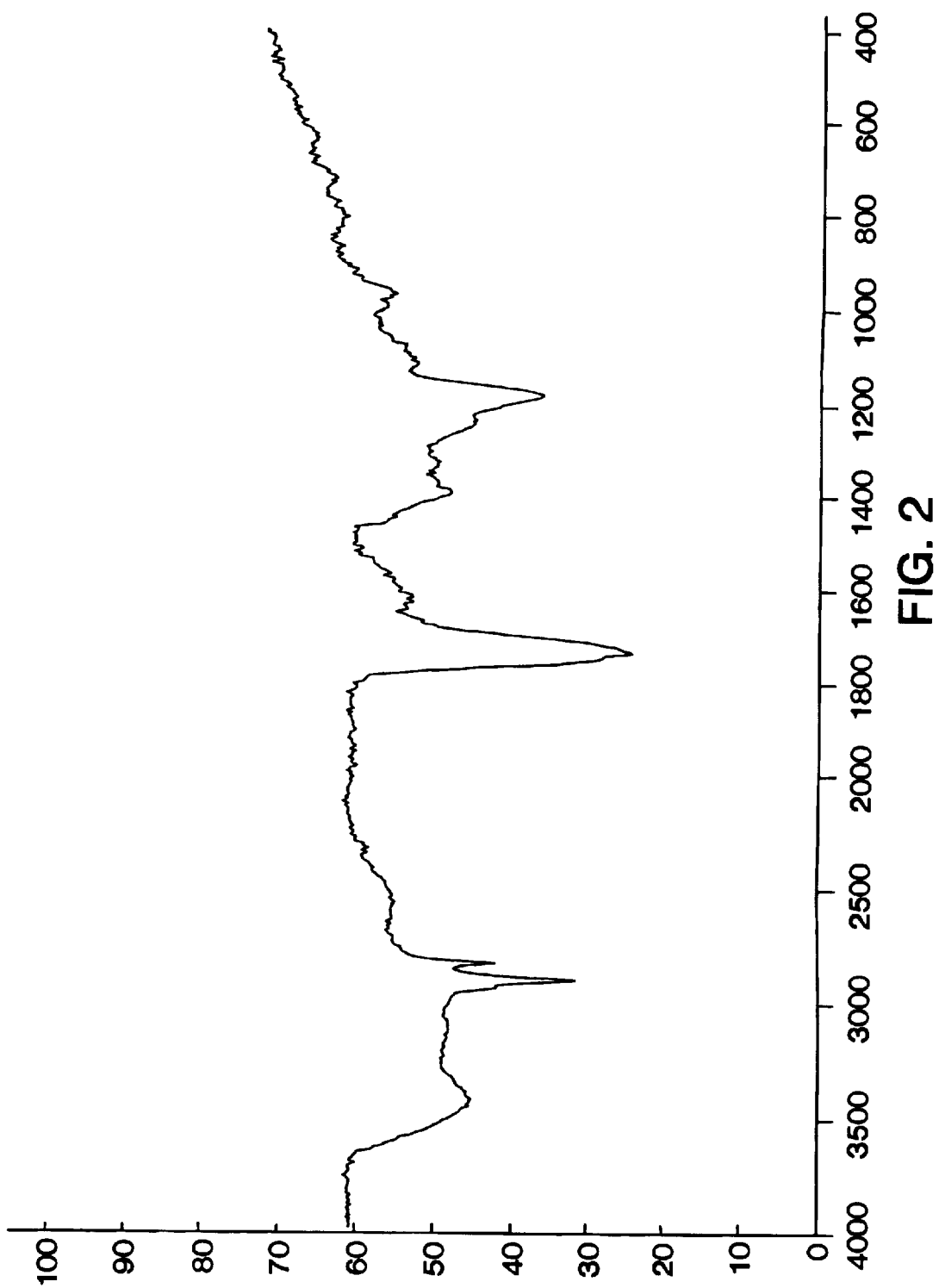
FIG. 2 is a chart showing the infrared absorption spectrum of the antifungal substance TKR1912-I, in which the abscissa represents wave number ($cm^{-1}$)

The UV spectrophotometric characterization in methanol of the purified white powdery product available upon vacuum concentration of the active fraction in the second high-performance liquid chromatography revealed the terminal absorption as shown in FIG. 1.

Figure 3:
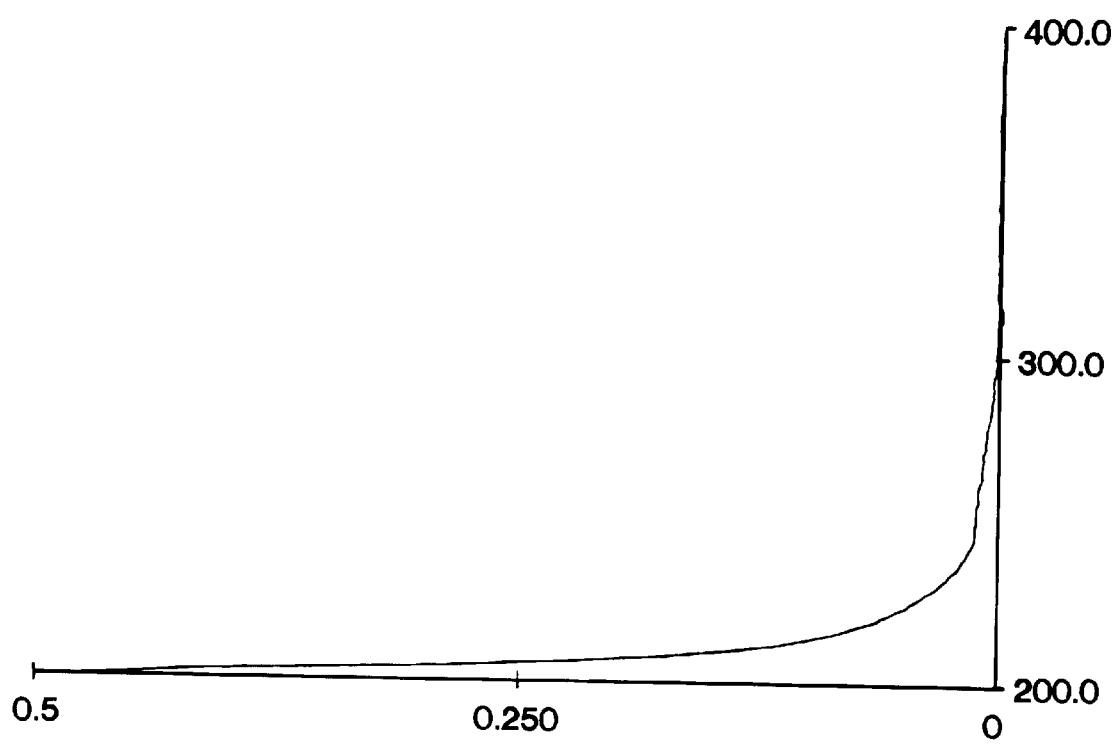
FIG. 3 is a chart showing the ultraviolet absorption spectrum of the antifungal substance TKR1912-II, in which the ordinate represents wavelength (nm)
Figure 4:
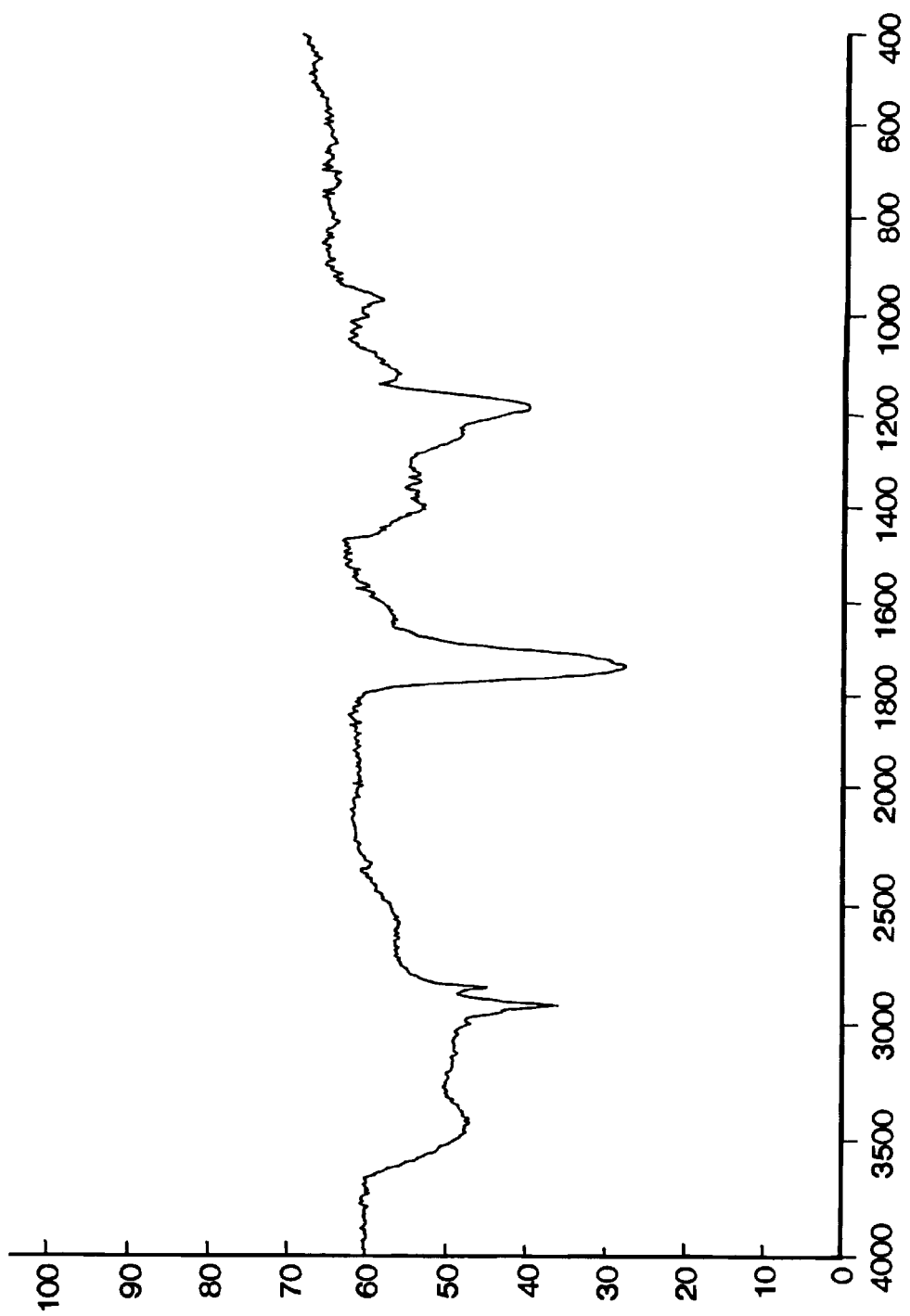
FIG. 4 is a chart showing the infrared absorption spectrum of the antifungal substance TKR1912-II, in which the abscissa represents wavenumbers ($cm^{-1}$)

The UV spectrophotometric characterization in methanol of the purified white powdery product available upon vacuum concentration of the active fraction in the first high-performance liquid chromatography revealed the terminal absorption as shown in FIG. 3.

(4) Infrared Absorption Spectra

The IR spectrophotometric (KBr method) characterization of the purified white powdery product available upon vacuum concentration of the active fraction in the second high-performance liquid chromatography revealed the following dominant absorption wavenumbers as shown in FIG. 2.

IR (KBr) (cm$^{-1}$): 3430, 2920, 2850, 1740, 1190

The IR spectrophotometric (KBr method) characterization of the purified white powdery product available upon vacuum concentration of the active fraction in the first high-performance liquid chromatography revealed the following dominant absorption wavenumbers as shown in FIG. 4.

IR (KBr) (cm$^{-1}$): 3440, 2920, 2850, 1740, 1200

Both of the above powders were soluble in methanol, chloroform, and water but practically insoluble in hexane.

Based on the above analyses, the purified white powdery product available upon vacuum concentration of the active fraction in the second high-performance liquid chromatography was identified to be TKR1912-I and the purified white powder product available upon vacuum concentration of the active fraction in the first high-performance liquid chromatography was identified to be TKR1912-II.

The above TKR1912-I and TKR1912-II were analyzed by reversed-phase partition high-performance liquid chromatography (HPLC) using LC-10A high-performance liquid chromatography (Shimadzu). This HPLC analysis was carried out under the following conditions.

Column: CAPCELLPAK $C_{18}$ (6 mm×150 mm) (Shiseido)
Mobile phase: 0.05% trifluoroacetic acid-containing 70% (v/v) acetonitrile/water
Column temperature: 40° C.
Detection UV wavelength: 220 nm As a result, the above TKR1912-I and TKR1912-II were eluted in the positions indicated in FIGS. 9 and 10, respectively.

(5) Determination of the Molecular Formulas and the Chemical Structural Formulas of TKR1912-I and TKR1912-II The $^{13}$C-NMR spectra of TKR1912-I and TKR1912-II showed that they had 26 and 28 carbon atoms, respectively, as described above. Together with these data, the high resolution FAB-MS of TKR1912-I, which gave the $[M+H]^+$ ion at m/z 559.2358, indicated its molecular formula to be $C_{26}H_{38}O_{13}$ (calculated for M+H, 559.2391). Also the high resolution FAB-MS of TKR1912-II, which gave the $[M+H]^+$ ion at m/z 585.2568, indicated its molecular formula to be $C_{28}H_{40}O_{13}$ (calculated for M+H, 585.2548). These molecular formulas were compatible with the $^{13}$C-NMR and $^1$H-NMR data.

Furthermore, from the $^{13}$C-NMR and $^1$H-NMR data and IR spectra, TKR1912-I has been found to have the following formula I:

(I)

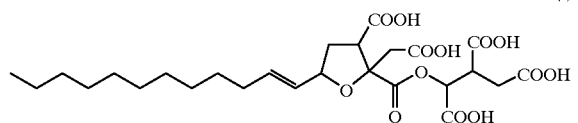

and TKR1912-II has been found to have the following formula II:

(II)

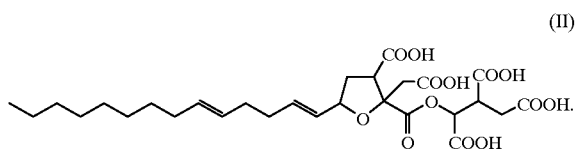

Biological Characteristics

The antifungal spectra of the above TKR1912-I and TKR1912-II against various microorganisms were determined. Using the liquid medium dilution method, the concentration causing a substantially complete inhibition of fungal growth was determined as minimal inhibitory concentration (μg/ml). The results are presented in Table 2. Moreover, the minimal concentration (μg/ml) causing partial growth inhibition was determined and the results are presented in parentheses in Table 2. In the table, YNBG stands for YNBG medium comprising 0.67% of yeast nitrogen base (Difco) and 1.0% of glucose and BHI stands for BHI medium comprising brain-heart infusion bouillon (Nissui Pharmaceutical).

TABLE 2

| Test strain | Medium | Minimal inhibitory concentration (μg/ml) | |
|---|---|---|---|
| | | TKR1912-I | TKR1912-II |
| Candida albicans TIMM0136 | YNBG | 3.13 (1.56) | 3.13 (0.78) |
| Candida kefyr TIMM0301 | YNBG | 12.5 (6.25) | 3.13 (1.56) |
| Cryptococcus neoformans TIMM0354 | YNBG | 6.25 | >100 (6.25) |
| Aspergillus fumigatus TIMM1776 | BHI | >100 (100) | >100 (25) |

It is apparent from Table 2 that TKR1912-I and TKR1912-II, the antifungal substances according to the present invention, are active against pathogenic fungi such as *Candida albicans, Candida kefyr, Cryptococcus neoformans*, etc.

Intraperitoneal administration of the TKR1912-I or TKR1912-II obtained above in a dose of 50 mg/kg to ICR mice caused no toxic signs in the animals.

INDUSTRIAL APPLICABILITY

As described above, the present invention provides the antifungal substances TKR1912-I and TKR1912-II which are of use in clinical medicine, for example in the therapy of fungal infections diseases, and a method for production of the substances.

What is claimed is:
1. TKR1912-I having the following formula I, or a parmacologically acceptable salt thereof:

(I)

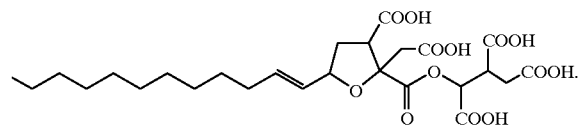

2. TKR1912-II having the following formula II, or a parmacologically acceptable salt thereof:

(II)

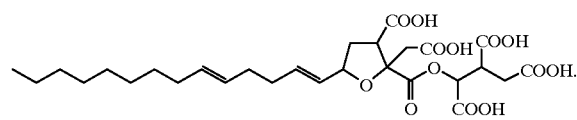

3. A microorganism belonging to the genus Aureobasidium and capable of producing either the antibiotic TKR1912-I or the antibiotic TKR1912-II or both.

4. The microorganism as defined in claim 3 wherein the microorganism is the Aureobasidium FERM BP-5368 or a spontaneous or artificial mutant of Aureobasidium FERM BP-5368.

5. A pharmaceutical composition comprising the antibiotic TKR1912-I or the antibiotic TKR1912-II or both in an effective antibiotic amount and a pharmaceutically acceptable carrier.

6. A method for treating a fungal infection disease which comprises administering an effective antibiotic amount of the antibiotic TKR1912-I or the antibiotic TKR1912-II or both to an animal or human being.

7. A method for inhibiting growth of fungus which comprises administering an effective antibiotic amount of the antibiotic TKR1912-I or the antibiotic TKR1912-II or both to a medium containing fungus.

* * * * *